(12) United States Patent
Höijer et al.

(10) Patent No.: US 7,047,073 B2
(45) Date of Patent: May 16, 2006

(54) CARDIAC STIMULATING DEVICE

(75) Inventors: Carl Höijer, Lund (SE); Hans Schüller, Lund (SE)

(73) Assignee: St. Jude Medical AB, Jarfalla (SE)

( * ) Notice: Subject to any disclaimer, the term of this patent is extended or adjusted under 35 U.S.C. 154(b) by 251 days.

(21) Appl. No.: 10/432,109

(22) PCT Filed: Nov. 15, 2001

(86) PCT No.: PCT/SE01/02548

§ 371 (c)(1),
(2), (4) Date: Oct. 30, 2003

(87) PCT Pub. No.: WO02/40097

PCT Pub. Date: May 23, 2002

(65) Prior Publication Data

US 2004/0064159 A1    Apr. 1, 2004

(30) Foreign Application Priority Data

Nov. 17, 2000   (SE) .................................... 0004240

(51) Int. Cl.
*A61N 1/362* (2006.01)
(52) U.S. Cl. ............................................. 607/9
(58) Field of Classification Search .................. 607/9, 607/14, 28
See application file for complete search history.

(56) References Cited

U.S. PATENT DOCUMENTS

| 4,856,524 A | 8/1989 | Baker, Jr. |
| 5,571,143 A | 11/1996 | Hoegnelid et al. |
| 5,720,768 A | 2/1998 | Verboven-Nelissen |
| 5,871,507 A | 2/1999 | Obel et al. |

FOREIGN PATENT DOCUMENTS

| EP | 0 494 487 | 7/1992 |
| WO | WO 99/55415 | 11/1999 |

OTHER PUBLICATIONS

"Proposal of a Method for Automatic Optimization of Left Heart Atrioventricular Interval Applicable to DDD Pacemakers," Chirife, PACE, vol. 18 (Jan. 1995) pp. 49-56.
Effects of Different Atrioventricular Intervals During Dual-Site Right Atrial Pacing on Left Atrial Mechanical Function, Ho et al. PACE, vol. 23, (Nov. 2000) pp. 1748-1751.

*Primary Examiner*—Scott M. Getzow
(74) *Attorney, Agent, or Firm*—Schiff Hardin LLP

(57) ABSTRACT

An implantable cardiac stimulating device has a pacing circuit connected via an electrode lead system to a first electrode which stimulates and detects activity in the left ventricle, a second electrode to stimulate and detect activity in the right atrium, and to a third electrode to detect activity in the left atrium. Upon the occurrence of a paced or sensed depolarization of the right atrium, a first AV-delay is started. When the subsequent left atrial depolarization is detected, a new AV-interval is started that is optimized for the left side of the heart. Either the left ventricle only, or both ventricles, is paced at the optimized left side AV-interval.

6 Claims, 2 Drawing Sheets

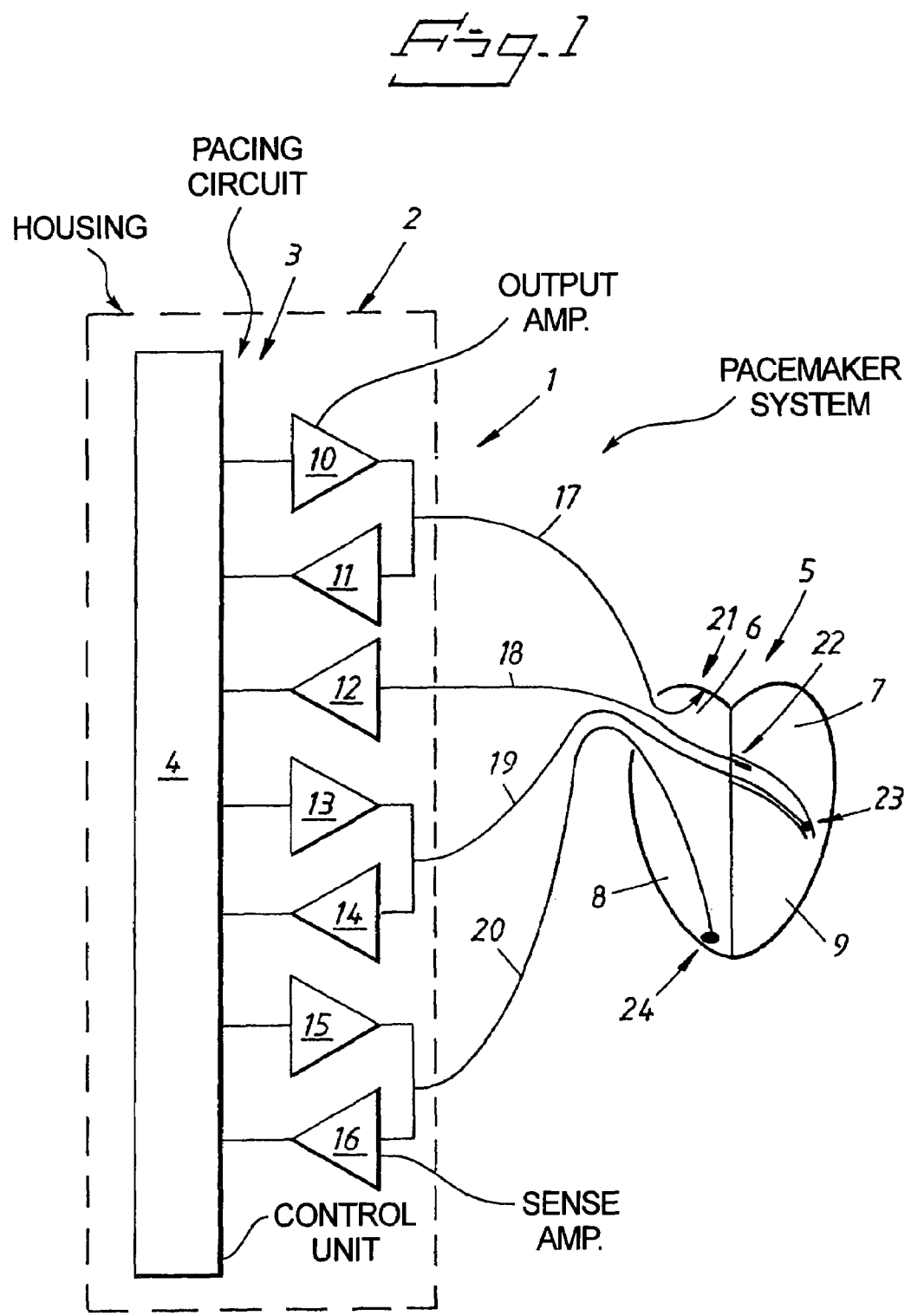

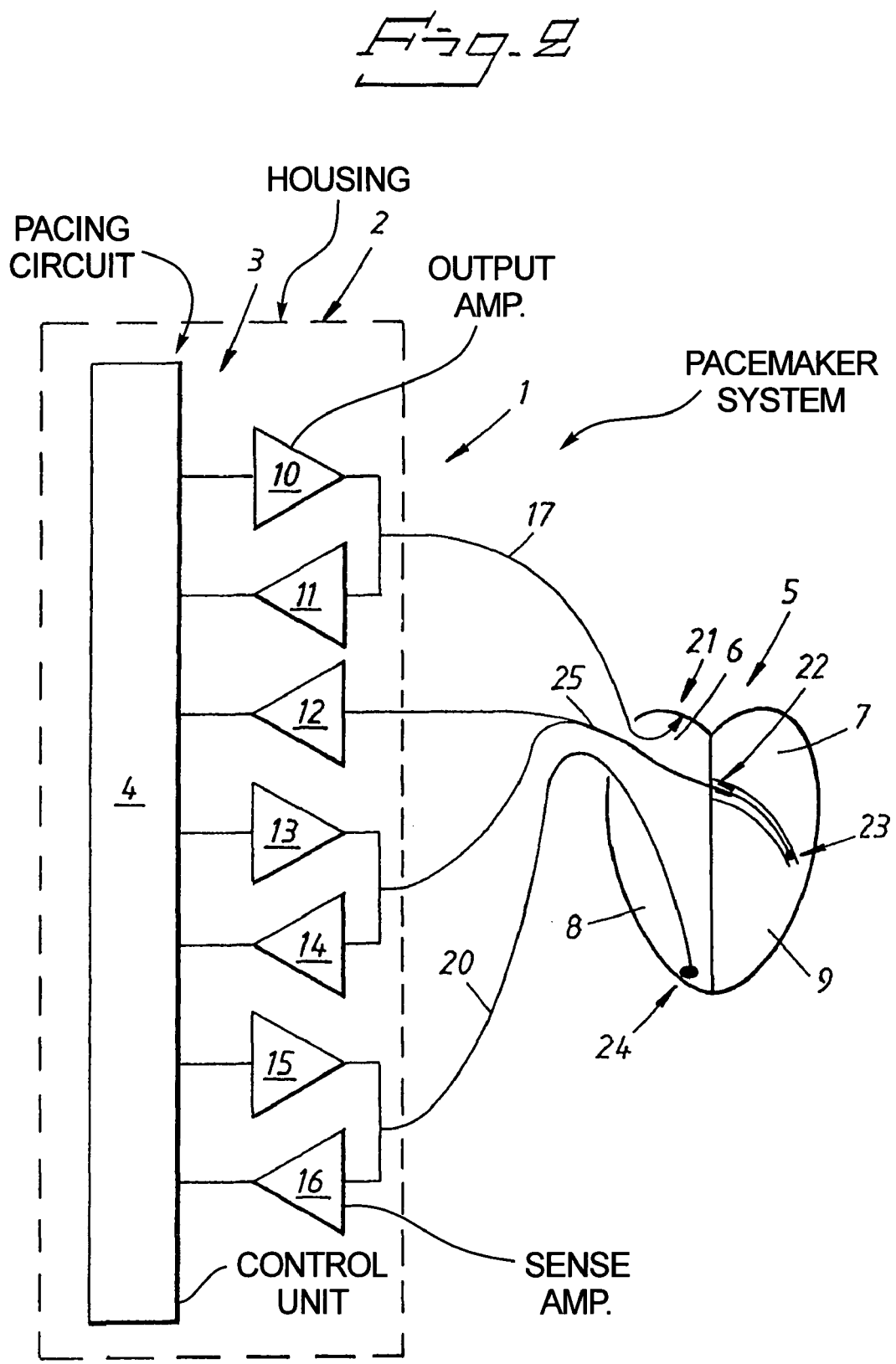

CARDIAC STIMULATING DEVICE

BACKGROUND OF THE INVENTION

1. Field of the Invention

The present invention relates to an implantable cardiac stimulating device of the type having the capability to sense and stimulate the right atrium, to sense the left atrium, and to sense and stimulate the right and left ventricles, respectively.

2. Description of the Prior Art

Most pacers are arranged to stimulate the right ventricle of the heart, but it is also known to stimulate the left ventricle. In particular for the treatment of congestive heart failure or other severe cardiac failures it is known to stimulate the left ventricle, or both ventricles, in order to optimize the hemodynamic performance of the heart.

U.S. Pat. No. 5,720,768 describes different possible electrode positions in order to stimulate or sense the different chambers of the heart. It is also disclosed that the conduction time from right atrium to left atrium may be observed and the left atrium may be paced if the conduction time is too long.

It is well known in the art that it is difficult to position an electrode to pace and sense the left atrium. There is a need to provide a device alleviating these difficulties.

SUMMARY OF THE INVENTION

An object of the present invention is to provide a cardiac pacemaker which provides an AV-interval which is optimized for the left side of the heart. This object is achieved in accordance with the invention in a cardiac stimulating device of the type initially described, wherein a first AV-interval is started at paced or sensed events occurring in the right atrium. When the atrial depolarization has conducted to the left atrium this is sensed through an electrode located in the coronary sinus, preferably the proximal portion thereof. At the detection of the left atrial depolarization a second AV-interval optimized for the left heart is started. When this AV-interval has elapsed the left ventricle is stimulated with the left heart AV-interval. If no atrial event is detected on the coronary sinus electrode the initially started first AV-interval, AV1, will be used. Thus the AV-interval for the left side of the heart is optimized without any need for stimulating the left atrium.

DESCRIPTION OF THE DRAWINGS

FIG. 1 is a schematic representation of a device according to the invention connected to a heart.

FIG. 2 is a schematic representation of a device according to the invention in which the leads have been integrated into one lead.

DESCRIPTION OF THE PREFERRED EMBODIMENTS

FIG. 1 shows an implantable cardiac stimulating device, hereinafter also called a pacemaker system 1, according to the invention. The pacemaker system 1 has a housing 2 and leads 17, 18, 19, 20. A pacing circuit 3 is enclosed in the housing 2. The pacing circuit 3 is adapted to be connected to lead 19 with electrode 23. FIG. 1 shows such an electrode 23 which is connected to the pacemaker via lead 19. The first electrode 23 is adapted to be positioned to stimulate the left ventricle 9 of the heart 5. The pacing circuit 13 is also adapted to be connected to a second electrode 22. FIG. 1 shows such a second electrode 22 connected to the pacing circuit 3 via a lead 18. The second electrode 22 is positioned to sense depolarizations of the left atrium of the heart 5. The pacing circuit 3 is further adapted to be connected to a third electrode 21. FIG. 1 shows such a third electrode 21 connected to the pacing circuit 13 via a lead 17. The third electrode 21 is positioned to sense depolarizations the right atrium of the heart 5.

The leads 17, 19 and 20 are appropriately connected to respective output amplifiers 12, 13 and 15 (which emit stimulation pulses) and the leads 17, 18 19 and 20 are connected to respective sense amplifiers 11, 12, 14, and 16. The amplifiers 10–16 are connected to a control unit 4. A sensed or paced event originating from the right atrial electrode 21 causes the control unit 4 to start a first AV-interval AV1. The first AV-interval AV1 may be set to optimize the PA-RV contraction, the RA-LV contraction or the RA-both RV,LV contraction in the absence of a LA sense. In the normal case this right atrial depolarization will be conducted to the left atrium and be sensed by sense amplifier 12 via lead 18 and electrode 22. When the depolarization is detected at the left atrium the first ongoing AV-interval AV1 is superseded by the control unit 4 with a second AV delay AV2, specifically optimized for the left side of the heart 5. This will provide a correct left side AV interval also if there is slow conduction from right atrium 6 to left atrium 7. If no P-wave is detected from left atrial electrode 22 then the initially started first AV-interval AV1 will be used. At the end of the first AV-interval AV1 a stimulation pulse is delivered to the left ventricle via lead the 19 and electrode 23.

The leads 17, 18, 19 and 20 may include more than one electrical conductor in order to allow for bipolar pacing and sensing. In that case electrodes 21, 22, 23, and 24 will have two active surfaces each.

In a preferred embodiment the system also has a lead 20 with electrode 24 for stimulation of the right ventricle S and for detection of R-waves from the right ventricle. In that case the right ventricle may be paced with an AV-delay optimized for the right heart and the left ventricle may be paced with an AV-delay optimized for the left heart. Alternatively both ventricles are paced synchronously with an AV-interval optimized for the left ventricle.

According to an alternative embodiment as shown in FIG. 2 leads 18 and 19 are integrated into one lead 25 comprising electrodes 23 and 22 for placement in left ventricle and left atrium respectively.

In still another embodiment differential sensing is applied between electrodes 23 and 22 and discrimination between left ventricular P-waves and R-waves is accomplished through analysis of timing and morphology of the differential signal. This sensing concept is described in U.S. Pat. No. 5,571,143 and in U.S. Pat. No. 5,871,507, the teaching of which are hereby incorporated herein by reference.

In still another embodiment the left atrial contraction is detected as a Far-Field P-Wave, FFPW, by sensing amplifier 14 via lead 19 and electrode 23. Morphology discrimination may be applied to discriminate between left ventricular R-waves and FFPW as described above. Upon detection of a FFPW the ongoing AV-interval is superseded by the second AV-delay AV2, that is started to provide an AV-delay optimized for the left side of the heart.

In a further refinement individual timing is provided for pacing the right and left ventricles. Right ventricle stimulation is delivered after the first AV-interval AV1 has elapsed. The second AV-interval AV2, which is started at the detection of a left atrial depolarization determines when the stimulation pulse shall be delivered to the left ventricle. If no left atrial depolarization is detected, the stimulation of the left ventricle is coordinated with the stimulation of the right ventricle.

Although modifications and changes may be suggested by those skilled in the art, it is the invention of the inventors to embody within the patent warranted heron all changes and modifications as reasonably and properly come within the scope of their contribution to the art.

We claim as our invention:

1. An implantable cardiac stimulating device comprising:
    a housing;
    a pacing circuit contained in said housing, said pacing circuit including a stimulating pulse generator arrangement for emitting stimulating pulses and an amplifying and sensing arrangement for sensing cardiac depolarizations;
    an electrode lead system connected to said pulse generator arrangement and to said amplifying and sensing arrangement, said electrode lead arrangement including a first electrode adapted for positioning to stimulate and sense depolarizations in a left ventricle of a heart, a second electrode adapted for positioning to sense depolarizations of a left atrium of the heart, and a third electrode adapted for positioning to stimulate and sense depolarizations in a right atrium of the heart; and
    said pacing circuit further including AV-delay optimization circuitry connected to said pulse generator arrangement and said amplifying and sensing arrangement, which starts a first AV-delay upon a sensed depolarization of the right atrium, and supercedes said AV-delay with a second AV-delay, optimized for a left side of the heart, upon sensing of a depolarization of the left atrium.

2. An implantable cardiac stimulating device as claimed in claim 1 wherein said electrode lead system further comprises an electrode adapted for positioning to stimulate and sense depolarizations in a right ventricle of the heart.

3. An implantable cardiac stimulating device as claimed in claim 2 wherein said pacing circuit controls said pulse generator arrangement to stimulate the right ventricle simultaneously with the left ventricle.

4. An implantable cardiac stimulating device as claimed in claim 2 wherein said pacing circuit controls said pulse generator arrangement to stimulate the right ventricle with an AV-interval optimized for a right side of the heart, starting with depolarization of the right atrium, and to stimulate the left ventricle with an AV-interval optimized for the left side of the heart, starting with detection of a depolarization in the left atrium, and if no depolarization in the left atrium is detected, to coordinate stimulation of the left ventricle with the stimulation of the right ventricle.

5. An implantable cardiac stimulating device as claimed in claim 1 wherein at least one of said first electrode, said second electrode and said third electrode is a bipolar electrode.

6. An implantable cardiac stimulating device as claimed in claim 1 wherein said second electrode detects a signal containing a far-field P-wave, and wherein said amplifying and sensing circuit senses said far-field P-wave as a depolarization in the left atrium.

* * * * *